United States Patent [19]

Yamamoto et al.

[11] 4,299,766
[45] Nov. 10, 1981

[54] PROCESS FOR PREPARING ALICYCLIC ISOCYANATES

[75] Inventors: Ryuichi Yamamoto; Yutaka Hirai; Akinobu Takagi; Zyunzi Tashima, all of Omuta, Japan

[73] Assignee: Mitsui Toatsu Chemicals, Inc., Tokyo, Japan

[21] Appl. No.: 170,333

[22] Filed: Jul. 21, 1980

[30] Foreign Application Priority Data

Jul. 20, 1979 [JP] Japan ................................. 54-91625

[51] Int. Cl.$^3$ .................. C07D 223/10; C07D 211/76; C07D 207/26
[52] U.S. Cl. ......................... 260/239.3 R; 260/326.45; 546/243
[58] Field of Search .................... 260/239.3 R, 326.45; 546/243

[56] References Cited

U.S. PATENT DOCUMENTS

| | | | |
|---|---|---|---|
| 2,698,845 | 1/1955 | Mastin et al. | 260/239.3 R |
| 2,822,373 | 2/1958 | Beck | 260/453 PH |
| 3,483,189 | 12/1969 | Brotherton et al. | 260/239.3 R |
| 3,591,635 | 7/1971 | Farrissey et al. | 252/413 |
| 3,856,862 | 12/1974 | Chung et al. | 564/451 |
| 3,987,033 | 10/1976 | Ojakaar | 260/239.3 R |
| 4,171,305 | 10/1979 | Mochizuki | 260/239.3 R |
| 4,191,833 | 3/1980 | Tucker | 260/239.3 R |
| 4,211,699 | 7/1980 | Winkelmann et al. | 260/239.3 R |

FOREIGN PATENT DOCUMENTS 1127338  9/1968  United Kingdom ......... 260/453 PH

OTHER PUBLICATIONS

Malz and Greenfield, "Industrial, Eng. Chem. Process. Res. Dev.", vol. 17, No. 4, (1978) p. 358.
Noller, "Chemistry of Organic Compounds", Second Edition (1957) (Saunders) pp. 479, 799 and 800.

*Primary Examiner*—Robert T. Bond
*Attorney, Agent, or Firm*—Sughrue, Mion, Zinn, Macpeak & Seas

[57] ABSTRACT

Lactam-blocked products of alicyclic isocyanates are obtained by blocking an aromatic isocyanate with lactam and subjecting the resulting blocked product to catalytic hydrogenation with use of a Rh catalyst.

The blocked alicyclic isocyanate obtained thus can be used, for example, as a curing agent for synthetic resins such as epoxy resins or as a starting material of urethane coatings.

The blocked isocyanate, if desired, may be subject to distillation whereby an alicyclic isocyanate is isolated by thermal dissociation and separation of the blocking agent.

4 Claims, No Drawings

PROCESS FOR PREPARING ALICYCLIC ISOCYANATES

BACKGROUND OF THE INVENTION

This invention relates to a process for the preparation of alicyclic isocyanates starting from the corresponding aromatic isocyanate.

Organic isocyanates are used widely as a material of polyurethane for foamed mold goods, elastomer coatings, adhesives and others and an intermediate of agricultural chemicals, medicines and the like. Among the organic isocyanates an aromatic diisocyanate is important for the polyurethane material and used in large quantities. However, since polyurethanes prepared from the aromatic isocyanates have a serious disadvantage of yellowing, they are unsuitable for the use in coatings. In this field a non-yellowing aliphatic diisocyanate or alicyclic isocyanate are solely used.

These organic isocyanates are produced in a commercial scale by reaction of the corresponding amine with phosgene. With the noticeable development of the polyurethan industry tolylene diisocyanate (hereinafter referred to as TDI) and diphenylmethanediisocyanate (hereinafter referred to as MDI) have been produced in large quantities and inexpensively and accordingly, the intermediates, i.e. tolylenediamine (hereinafter referred to as TDA) and diaminodiphenylmethane (hereinafter referred to as MDA) have become available inexpensively and easily. Thus, starting from these aromatic diamines, the corresponding alicyclic amine has been prepared by hydrogenation reaction, from which an alicyclic isocyanate has been then prepared by the reaction with phosgene as disclosed in, for example, U.S. Pat. No. 3,856,862, No. 3,591,635, No. 2,822,373 and G.B. Pat. No. 1,127,338.

However, owing to the two steps of the hydrogenation of the aromatic nucleus and the reaction with phosgene, the preparation of alicyclic isocyanates is expensive as compared with the preparation of TDI and MDI. In this way the demand for these alicyclic isocyanates is limited because of the high preparation cost.

SUMMARY OF THE INVENTION

An object of this invention is to provide a process for preparing alicyclic isocyanates by a simplified step and in an economical convenience, starting from aromatic isocyanates.

In accordance with this invention, there is provided a process for the preparation of lactam-blocked products of alicyclic isocyanates which comprises blocking an aromatic isocyanate with lactam and subjecting the blocked product obtained to catalytic hydrogenation with use of a rhodium catalyst thereby to obtain blocked product of the corresponding alicyclic isocyanate.

The blocked alicyclic isocyanate can be used, for example, as a curing agent for synthetic resins such as epoxy resins or as a starting material of urethane coatings without requiring any separation and purification.

The blocked isocyanate, if desired, may be subject to distillation whereby an alicyclic isocyanate is isolated by thermal dissociation and separation of the blocking agent.

DETAILED DESCRIPTION OF THE INVENTION

The aromatic isocyanates which may be used in this invention are aromatic polyisocyanates such as TDI, MDI, diphenyletherdiisocyanate, 1,5-naphthalenediisocyanate, phenylenediisocyanate and the like or aromatic monoisocyanates such as phenylisocyanate, tolylisocyanate and the like.

The lactams which may be used as a blocking agent are 2-pyrrolidone, ε-caprolactam, ω-laurolactam and the like and particularly, 2-pyrrolidone and ε-caprolactam are preferred.

The blocking of aromatic isocyanates may be carried out in known conditions by conventional methods.

Next, the hydrogenation reaction of the blocked isocyanate is carried out using a Rh catalyst. It is preferred that the reaction is carried out in a relatively low temperature so that no thermal dissociation of the blocked isocyanate takes place. A rhodium catalyst is conveniently used for the hydrogenation at a relatively low temperature. The suitable reaction temperature is comprised between 50° and 150° C., preferably 50°-120° C. With high temperature the thermal dissociation accompanied by side reactions takes place and therefore, the catalyst is inactivated.

The catalyst may be rhodium of 0.05%-20% by weight, preferably 0.2%-10% by weight supported on a carrier such as activated carbon, carbon black, alumina, diatom earth and others. A commercially available Rh catalyst may be also used. The preparation method of the catalyst is disclosed in, for example, U.S. Pat. No. 3,591,635. The amount of Rh metal to be used (exclusive of the carrier) may be about 0.05%-3%, preferably 0.2%-2.0% by weight based on the amount of the blocked isocyanate present in the reaction mixture.

The hydrogenation reaction may be usually carried out in an organic solvent. Preferred solvents are alcohols such as methanol, ethanol, propanol, butanol, pentanol, hexanol, heptanol, octanol or ethyleneglycol, dioxane, tetrahydrofuran, ethers, cellosolves, organic acid esters and others. The amount of the solvent is within the range of 5%-50% in concentration in the reaction mixture of the blocked isocyanate, though it is unnecessary to add such an amount that the blocked isocyanates are completely dissolved. The hydrogen pressure in the hydrogenation may vary within the range of about 10-250 atms., though preferred hydrogen pressures are between 30 and 100 atms.

After hydrogenation the catalyst is removed by, for example, filtration from the reaction product solution and then, the solvent is separated by, for example, distillation whereby the corresponding blocked alicyclic isocyanates are obtained. These blocked isocyanates have little tar-like high polymers as by-products and accordingly, can be used, as they are, for, e.g. a curing agent for synthetic resins such as epoxy resins or a material for urethane coatings without requiring any purification.

For the purpose of obtaining alicyclic isocyanates the blocked isocyanates are subject to distillation whereby the blocking agent is removed by thermal dissociation and fractionation to isolate alicyclic isocyanates. The distillation may be conducted in known conditions by conventional methods. By way of CHMDI the blocked products are charged into a distiller provided with a packed tower and heated at 150°-250° C. under reduced pressure (e.g. 5 mmHg) and then, the blocking agent is distilled off by thermal dissociation. Next, the degree of vacuum is elevated to 1-2 mmHg and then, CHMDI is distilled off at temperatures of 165°-180° C. For the purpose of preventing isocyanates from thermal polymerization, the distillation may be, preferably, carried out in the presence of a high boiling solvent.

The alicyclic isocyanates thus obtained can be used in the same uses as those obtained by the conventional method, e.g. for a non-yellowing urethan coating.

The recovered blocking agent can be used repeatedly.

According to this invention, the blocked isocyanates are obtained starting from aromatic isocyanates such as MDI and TDI which are available inexpensively and the corresponding blocked alicyclic isocyanates are formed in one step by the hydrogenation to the aromatic nucleus. Further, alicyclic isocyanates are obtained in a simplified operation by distillation of the blocked isocyanate thereby removing the blocking agent. Thus this invention requires no complicated operations of hydrogenating aromatic amines and reacting with phosgene as in the conventional method.

Also, since a Rh catalyst can be used repeatedly for hydrogenation, the preparation process using the expensive Rh may be effected economically.

Dicyclohexylmethanediisocyanate (hereinafter referred to as CHMDI) obtained by hydrogenation of the blocked MDI is a mixture of stereoisomers of trans-trans, trans-cis and cis-cis, which is much in the trans-cis and cis-cis isomers as compared with CHMDI obtained by the conventional method consisting of hydrogenation of MDA and reaction with phosgene. Thus, the CHMDI according to this invention exhibits liquid at normal temperature or is of low-melting point and accordingly, is easy to handle as a material of coatings which result in good properties of coated film.

This invention will be illustrated by the following non-limitative Examples.

EXAMPLE 1

(1) Synthesis of blocked isocyanate

Into a 1.0 l, four-necked flask equipped with a thermometer, a stirrer, a condenser and a dropping funnel were 186.9 g of a previously dried toluene and 124.6 g (1.1 mols) of ε-caprolactam charged and ε-caprolactam was completely dissolved at 60° C.

Next, a solution of 125 g (0.5 mols) of MDI dissolved in 187.5 g of a dried toluene was added from the dropping funnel over about 30 minutes and a blocking reaction was conducted at 60°-80° C. for 6 hours. After determining the disappearance of non-reacted isocyanates by analysis, the reaction product solution was cooled to room temperature and the deposits were filtered, which were then washed with water to remove an excess of ε-caprolactam. After drying 232.3 g (0.49 mols) of ε-caprolactam-blocked MDI were obtained.

(2) Hydrogenation reaction 30.5 g (0.064 mols) of the above lactam-blocked MDI, 250 ml of isopropanol and 3.05 g of a 5% Rh/activated carbon catalyst (manufactured by Nihon Engelhard Comp.) were charged into a 500 ml autoclave and hydrogenation was carried out at 70°-80° C. under hydrogen pressure of 50 atms. After 68 minutes the taking-up of hydrogen stopped when the amount of hydrogen taken up had reached the theoretical value.

Then the hydrogenation was discontinued and after cooling the room temperature, the reaction product mixture was taken out, which was then filtered to remove the catalyst. The filtrate was subject to distillation to remove isopropanol and then, products of white solid were deposited in the distiller. The solids thus obtained after milling and drying was 30.6 g (0.0626 mols) in weight and 97.9% in yield based on the weight of the blocked MDI.

Analysis on this product was as follows:

|  | C | H | N |
|---|---|---|---|
| Calculated, %: as $C_{27}H_{44}N_4O_4$ | 66.39 | 9.01 | 11.48 |
| Found, % | 66.05 | 9.03 | 11.36 |

Using the recovered catalyst repeatedly five times, the same hydrogenation was carried out. As a result there was little change in the hydrogenation time, the yield and quality of the end product.

(3) Distillation

Into a 500 ml, four-necked flask equipped with a packed tower (McMahon packing 25φ×300 mm packed), a thermometer and a nitrogen blowing conduit were charged 100 ml of a paraffin hydrocarbon solvent (B.P.>303° C./10 mmHg abs., Nuray N-165AH, the tradename by Esso) and 60 g (0.123 mols of the above (2) product and subjected to distillation under reduced pressure of 5 mmHg abs. and the fractions up to 130° C. were distilled off. Thereafter the pressure was reduced to 1.0 mmHg abs. and 24.1 g (0.092 mols) of the distillates of from the boiling point 165° to 180° C. were obtained. The distillates exhibit a semi-liquid (including crystals) of colorlessness and transparency at room temperature (25° C.) and as a result of analysis the purity from the percentage of NCO was 95%. The IR analysis also showed that the spectrogram was consistent with that of a commercially available 4,4'-dicyclohexylmethanediisocyanate (Heylene W, the tradename by E. I. du Pont). Yield: 75% by weight Elementary analysis on this product as as follows:

|  | C | H | N |
|---|---|---|---|
| Calculated, % as $C_{15}H_{22}N_2O_2$ | 68.70 | 8.40 | 10.69 |
| Found, % | 68.58 | 8.35 | 10.51 |

Also, the isomer ratios were as follows:

| Trans-trans isomer | 32.1% |
|---|---|
| Trans-cis isomer | 18.5% |
| Cis-cis isomer | 49.4% |

For comparison, according to the conventional method, MDA was subject to hydrogenation and the obtained CHMDA was reacted with phosgene to synthesize CHMDI. The CHMDI obtained has a freezing point of 50.9° C. and the isomers and the ratios thereof are as follows:

| Trans-trans isomer | 53.4% |
|---|---|
| Trans-cis isomer | 7.3% |
| Cis-cis isomer | 39.3% |

EXAMPLE 2

206.4 g of a 2-pyrrolidone-blocked MDI were obtained in the same manner as in Example 1 except using 93.6 g (1.1 mols) of 2-pyrrolidone instead of ε-caprolactam. Yield: 98.2%

Hydrogenation reaction was carried out in the same manner as in Example 1 and after about 92 minutes the taking-up of hydrogen stopped. Similarly, after the procedure 30.7 g (0.071 mols) of solid were obtained, which were of 98.3% in yield based on the weight of the blocked MDI (30.5 g).

An elementary analysis on this product was as follows:

|  | C | H | N |
|---|---|---|---|
| Calculated, % as $C_{23}H_{36}N_4O_4$ | 63.89 | 8.33 | 12.96 |
| Found | 66.25 | 8.21 | 12.70 |

Distillation was carried out in the same manner as in Example 1 and 28.7 g of CHMDI were obtained with a purity of 97%. Thus a yield of 79% was obtained from 60 g (0.139 mols) of the blocked isocyanate.

EXAMPLE 3

196.3 g of a ε-caprolactam-blocked product of 2,4-tolylenediisocyanate were obtained in the same manner as in Example 1 except using 87 g of 2,4-tolylenediisocyanate instead of MDI.

Using the blocked product obtained, the hydrogenation to the aromatic nucleus was carried out in the same manner as in Example 1. After about 130 minutes the taking-up of hydrogen stopped when the amount of hydrogen taken up had reached the theoretical value. Thereafter the hydrogenation reaction product was taken out in the same procedure as in Example 1 and was 30.3 g in weight.

An elementary analysis on this product was as follows:

|  | C | H | N |
|---|---|---|---|
| Calculated, % as $C_{21}H_{34}N_4O_4$ | 62.07 | 8.37 | 13.79 |
| Found, % | 61.98 | 8.26 | 13.66 |

What is claimed is

1. A process for the preparation of lactam-blocked products of alicyclic isocyanates, comprising the steps of:
    (a) blocking an aromatic isocyanate with lactam, wherein said aromatic isocyanate is selected from the group consisting of tolylene diisocyanate diphenylmethanediisocyanate 1,5-naphthalenediisocyanate phenylene diisocyanate phenylisocyanate or tolylisocyanate, and wherein said lactam is selected from the group consisting of 2-pyrrolidone, ε-caprolactam or ω-laurolactam; and
    (b) subjecting the blocked product to catalytic hydrogenation with a catalyst containing 0.05% to 20% by weight rhodium, at 50° to 150° C., in the presence of a solvent in an amount of 5% to 50%, in a hydrogen pressure atmosphere of about 10 to 250 atmospheres, in order to obtain the blocked product of the corresponding alicyclic isocyanate.

2. A process as claimed in claim 1, further including the step of:
    (c) subjecting the blocked isocyanate obtained to distillation in order to effect thermo disassociation and separation of the blocking agent.

3. The process as claimed in any of claims 1 or 2 wherein said aromatic isocyanate is 4,4'-diphenylmethanediisocyanate, 2,4-tolylenediisocyanate or 2,6-tolylenediisocyanate or a mixture of 2,4-tolylenediisocyanate and 2,6-tolylenediisocyanate.

4. The process as claimed in any of claims 1 or 2 wherein the lactam as the blocking agent is 2-pyrrolidone or ε-caprolactam.

* * * * *